United States Patent
Hotier et al.

(10) Patent No.: US 8,123,951 B2
(45) Date of Patent: Feb. 28, 2012

(54) PROCESS AND APPARATUS FOR SIMULATED MOVING BED SEPARATION COMPRISING BYPASS LINES IN EVERY OTHER BED AND WITH CONTROLLED FLUSHING FLOW RATES DURING INJECTIONS AND WITHDRAWALS

(75) Inventors: Gerard Hotier, Rueil Malmaison (FR); Damien Leinekugel Le Cocq, Lyons (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 0 days.

(21) Appl. No.: 13/025,316

(22) Filed: Feb. 11, 2011

(65) Prior Publication Data

US 2011/0315634 A1    Dec. 29, 2011

(30) Foreign Application Priority Data

Feb. 11, 2010    (FR) ...................... 10 00571

(51) Int. Cl.
    *B01D 15/08* (2006.01)
(52) U.S. Cl. ..... 210/659; 210/635; 210/656; 210/198.2; 585/825; 585/828
(58) Field of Classification Search .................. 210/635, 210/656, 659, 662, 198.2; 585/825, 828
    See application file for complete search history.

(56) References Cited

U.S. PATENT DOCUMENTS

| 5,882,523 | A | 3/1999 | Hotier et al. |
| 5,972,224 | A * | 10/1999 | Hotier et al. .................. 210/659 |
| 6,110,364 | A * | 8/2000 | Hotier et al. ............... 210/198.2 |
| 6,261,458 | B1 | 7/2001 | Callebert et al. |
| 6,284,200 | B1 | 9/2001 | Hotier |
| 6,537,451 | B1 * | 3/2003 | Hotier ........................ 210/198.2 |
| 6,797,175 | B2 * | 9/2004 | Hotier .......................... 210/659 |
| 2008/0121586 | A1 | 5/2008 | Hotier et al. |
| 2010/0048973 | A1 * | 2/2010 | Decoodt et al. ............... 585/822 |
| 2010/0258505 | A1 * | 10/2010 | Decoodt et al. ............... 210/661 |
| 2011/0201865 | A1 * | 8/2011 | Decoodt et al. ............... 585/822 |

FOREIGN PATENT DOCUMENTS

| EP | 0 821 988 A1 | 2/1998 |
| EP | 0 846 483 A1 | 6/1998 |
| EP | 1 913 988 A1 | 4/2008 |

OTHER PUBLICATIONS

Search Report of FR 1000571 (Aug. 31, 2010).

* cited by examiner

*Primary Examiner* — Ernest G Therkorn
(74) *Attorney, Agent, or Firm* — Millen, White, Zelano & Branigan, P.C.

(57) ABSTRACT

A process for separating a feed F by simulated moving bed adsorption in a SMB device comprises external bypass lines $L_{i/i+1}$ which directly connect two successive plates, $P_i$, $P_{i+1}$, the index "i" being either even or (exclusive of the foregoing) odd, along the whole length of the column, allowing said plates to be flushed, in which each of the bypass lines $L_{i/i+1}$ comprises automated means for regulating the flow rate in the bypass lines, the bypass lines in certain cases being subject to a flushing flow during injection or withdrawal operations.

5 Claims, 4 Drawing Sheets

(a)    (b)    (c)

PROCESS AND APPARATUS FOR SIMULATED MOVING BED SEPARATION COMPRISING BYPASS LINES IN EVERY OTHER BED AND WITH CONTROLLED FLUSHING FLOW RATES DURING INJECTIONS AND WITHDRAWALS

FIELD OF THE INVENTION

The invention relates to the field of separations of natural or chemically produced products which are difficult to separate by distillation. A family of processes and associated devices is used, known as simulated moving bed processes or separation devices, either in simulated counter-current or in simulated co-current mode, which will hereinafter be known by the generic term "SMB".

The fields concerned are particularly but not exclusively:
- separation of normal paraffins from branched paraffins, napthenes and aromatics;
- olefin/paraffin separation;
- separation of para-xylene from other aromatic C8 isomers;
- separation of meta-xylene from other aromatic C8 isomers
- separation of ethylbenzene from other aromatic C8 isomers.

Many other applications exist beyond the refinery and petrochemicals complex; those which may be cited include glucose/fructose separation, the separation of positional isomers of cresol, separation of optical isomers, etc.

PRIOR ART

SMB separation is well known in the art. As a general rule, a column operating in simulated moving bed mode comprises at least three operating zones, and optionally four or five operating zones, each of said zones being constituted by a certain number of successive beds, and each zone being defined by its position included between a supply point and a withdrawal point. Typically, a SMB column is supplied by at least one feed F to be fractionated and a desorbant D (sometimes termed the eluent), and at least one raffinate R and an extract E are withdrawn from said column.

The supply and withdrawal points are regularly shifted over time, in the same direction and retaining their relative position, by a value corresponding to one bed. The time interval separating two successive shifts of the supply and withdrawal points is termed the period.

By definition, each of the operational zones is designated by a number:
- zone 1=zone for desorption of compounds in the extract, included between injection of the desorbant D and removal of the extract E;
- zone 2=zone for desorption of compounds in the raffinate, included between the removal of the extract E and the injection of the feed to be fractionated F;
- zone 3=zone for adsorption of the compounds in the extract, included between the injection of the feed and the withdrawal of the raffinate R;
- and preferably a zone 4 located between the withdrawal of the raffinate and the injection of the desorbant.

The prior art describes in detail various devices and processes for carrying out simulated moving bed feed separation.

Patents which may in particular be cited are U.S. Pat. No. 2,985,589, U.S. Pat. No. 3,214,247, U.S. Pat. No. 3,268,605, U.S. Pat. No. 3,592,612, U.S. Pat. No. 4,614,204, U.S. Pat. No. 4,378,292, U.S. Pat. No. 5,200,075, U.S. Pat. No. 5,316,821. Those patents also describe the function of an SMB in detail.

SMB devices typically comprise at least one column (and frequently two) divided into several successive beds of adsorbant $A_i$, said beds being separated by plates $P_i$, each plate $P_i$ comprising one, two or four chambers which can carry out sequential operations of supply of the feed or injection of the desorbant and extraction of the raffinate or extract.

The present invention comes into the category of single-chamber devices, i.e. which can carry out both supply and withdrawal of the various streams using said chamber.

As will be described in more detail below, the plates are generally divided into panels, and each panel comprises a chamber for supply and withdrawal of streams.

Each of the plates $P_i$ typically comprises a plurality of distributor-mixer-extractor panels termed "DME plates" supplied via distribution/extraction lines or systems. The plates may be of any type and any geometry.

The plates are generally divided into panels corresponding to adjacent sectors in the section of the column, for example panels with angular sectors such as those described in U.S. Pat. No. 6,537,451, FIG. 8, or panels with parallel sectors such as those described in U.S. Pat. No. 6,797,175.

Preferably, the separation column of the invention comprises DME plates of the type with parallel sectors and di-symmetrical supplies.

Distribution over each of the beds requires that the principal stream originating from the preceding bed be collected, that a supplemental fluid or secondary fluid be capable of being injected while mixing the two fluids as much as possible, or it requires that a portion of the collected fluid should be capable of being removed, of being extracted to send it out of the device and also a fluid should be capable of being re-distributed over the next bed.

A generic problem with all SMB devices is that of minimizing the pollution generated by the liquid found in the various zones of the circuit or circuits for supplying and withdrawing fluids to or from the plates during modifications of the supply and withdrawal points during operation of the SMB.

When during the operational sequence a line, chamber or supply zone for a plate $P_i$ is no longer flushed by a process fluid, it becomes a dead zone in which the liquid stagnates, and it is only moved again when another process fluid moves in it once more. The operation of the SMB means that this is a process fluid which is a different fluid from the fluid stagnating in the line under consideration.

The mixing or the movement over a brief time interval of fluids with substantially different compositions introduces perturbations into the concentration profile of the zone under consideration compared with the ideal operation, for which compositional discontinuities should be avoided.

Another problem resides in possible re-circulation between the various zones of the same plate, and more generally over the whole of the distribution/extraction system of the same plate, due to very small pressure differences between the various zones of the plate; this induces further perturbation compared with ideal operation.

In order to overcome these problems due to re-circulation and to dead zones, various solutions are known in the prior art:
a) a proposal has already been made to flush the distribution/extraction system of a given plate using desorbant or the relatively pure desired product. That technique avoids pollution of the desired product during its extraction. However, since the flushing liquid has a very different composition from the liquid it displaces, this introduces compositional discontinuities which are prejudicial to ideal operation. This first flushing variation typically carried out flushes of short duration with a high concentration gradient. Such flushes are of short duration precisely in order to limit the effects of compositional discontinuities.

b) As described in U.S. Pat. No. 5,972,224 and U.S. Pat. No. 6,110,364, another solution consists of passing a majority of the principal stream into the interior of the column and a minority of that stream (typically 1% to 20% of the principal stream) outwardly via external bypass lines between successive plates. This flushing of the distribution/extraction system at one plate by a stream deriving from the plate above is typically carried out continuously, so that the lines and zones of the distribution/extraction system are no longer "dead" but are constantly flushed.

Such a system with continuous flushing via bypass lines is disclosed in FIG. 2 of patent FR-2 772 634. The diameter of the bypass lines is generally small and the lines include a small diameter valve which reduces the cost of the system.

According to the teaching of U.S. Pat. No. 5,972,224 and U.S. Pat. No. 6,110,364, the distribution/extraction system of a given plate is intended to be flushed with a liquid having a composition very close to that of the displaced liquid (liquid present in the distribution system or moving on a plate). Thus, mixing of fluids with different compositions is minimized, and compositional discontinuities are reduced.

To this end, U.S. Pat. No. 5,972,224 and U.S. Pat. No. 6,110,364 recommend using flush flow rates in the bypass lines such that the rate of transit in each bypass line is substantially the same as the rate of advance of the concentration gradient in the principal stream of the SMB. This is then termed "synchronous" flushing or "synchronicity flow rate" flushing. Thus, the various lines and volumes are flushed by a fluid which has a substantially identical composition to that of the liquid therein, and the liquid moving in a bypass line is re-introduced at a point where the composition of the principal stream is substantially identical.

The flushes are thus synchronous and with a low or zero concentration gradient.

According to the teaching of that patent, a flush is termed "synchronous" when the flush flow rate $QS_{i/i+1}$ originating from one plate $P_i$ to the next plate $P_{i+1}$ is equal to V/ST in which V is the cumulative volume of the distribution systems of the plates $P_i$ (i.e. $V_i$) and $P_{i+1}$ (i.e. $V_{i+1}$) and of the volume of the bypass line between said two plates (i.e. $VL_{i/i+1}$), and ST is the switch time of the SMB between two successive switches of the supplies/extractions.

Thus, we have:

$$\text{Synchronicity flow rate} = QS_{i/i+1} = (V_i + V_{i+1} + VL_{i/i+1})/ST,$$

where:

$QS_{i/i+1}$ = flow rate of flush originating from plate $P_i$, moving towards the next (typically lower) plate $P_{i+1}$;

$V_i$ = volume of distribution/extraction system of outflow plate $P_i$;

$V_{i+1}$ = volume of distribution/extraction system of inflow plate $P_{i+1}$;

$VL_{i/i+1}$ = volume of bypass line between $P_i$ and $P_{i+1}$;

ST = switch time.

Synchronous flushing is typically carried out by flushing at a controlled rate, adapted to each of the zones, of 50% to 150% of the synchronicity flow rate in said zones, and ideally 100% of the synchronicity flow rate. The flow rates in the bypass lines of the 4 zones of the SMB are controlled by regulating means in each bypass line.

As an example, the skilled person could use a flow rate of 90% of the synchronicity flow rate in all of these zones, or 110%, or even any other value close to 100% of the synchronicity flow rate. However, provided that regulating means exist, the skilled person, following the teaching of the patent cited above, will naturally elect to control the flow rates in the 4 zones in a manner which corresponds exactly to the synchronicity flow rate (100% of the synchronicity flow rate).

One example of a SMB separation device of great industrial importance concerns the separation of aromatic C8 cuts with a view to producing para-xylene of commercial purity, typically at least 99.7% by weight, and a raffinate rich in ethylbenzene, ortho-xylene and meta-xylene.

The two preceding cited implementations can achieve the aim of commercial purity. However, the Applicant has demonstrated that while the teaching of the "synchronous flushes" of U.S. Pat. No. 5,972,224 and U.S. Pat. No. 6,110,364 constitutes a distinct improvement over the prior art, it is surprisingly possible to further improve the operation and performance of the simulated moving bed separation process by refining the rules defining the various flow rates of the bypass lines.

Finally, application 08/04637 describes a bypass line device, the lines connecting all of the plates $P_i$, $P_{i+1}$ without distinguishing the parity of the index "i", with a rule concerning the flow rates to be applied to each line, which rule is different depending on whether there is at least one closed bypass line on the zone under consideration or whether all of the bypass lines are open.

According to application 08/04637, it is stated that "several reasons may result in closure of a bypass line in a given zone. In particular, when a fluid (feed or desorbant) is injected into a plate $P_i$, an injection line is used. That line is connected to a bypass line connected to said plate, i.e. either the bypass line $L_{i-1/i}$ or the bypass line $L_{i/i+1}$. Irrespective of which bypass line is connected to the injection line employed, it is then necessary to close said line by means of an on-off valve, a flow regulating valve or a non-return valve, or by any other technique means that can stop the flow in order to ensure that the injected fluid flows properly towards the plate $P_i$.

In the same manner, when withdrawing an effluent (extract or raffinate) from a plate $P_i$, a withdrawal line is used. This withdrawal line is connected to a bypass line connected to said plate, i.e. either the bypass line $L_{i-1/i}$ or the bypass line $L_{i/i+1}$. Irrespective of which bypass line is connected to the withdrawal line employed, it is then necessary to close said line by means of an on-off valve, a flow regulating valve or a non-return valve, or by any other technique means that can stop the flow to ensure that fluid is correctly withdrawn from the plate $P_i$."

In the present application, the bypass lines will not be systematically closed during injection or withdrawal operations, i.e. more precisely, when said bypass lines are connected to injection lines or withdrawal lines in operation.

Application 09/01784 is an improvement to application 08/04637 insofar as the flow rate rules to be applied to each bypass line are defined for each of the various operational zones of the column. That application 09/01784 concerns a particular configuration of the bypass lines which connect two successive plates, the first plate having an even index or, in an exclusive manner, having an odd index, as described in patents FR-2 904 776 and FR-2 913 345.

The present application is an improvement to application 09/01784 in that:

firstly, the bypass lines are not systematically closed during the injection or withdrawal operations, i.e. more precisely, when said bypass lines are connected to injection or withdrawal lines which are operating;

and secondly, the rules for managing the flow rates are for application to the bypass lines during the injection or withdrawal operations.

The present invention concerns a particular configuration of the bypass lines which connect two successive plates, the first plate having an even index or, in an exclusive manner, having an odd index.

The connections to the injection lines are located upstream of the connections to the withdrawal lines. Between the connections to the injection lines and the connections to the withdrawal lines is a regulating valve $V_{i/i+1}$. The bypass line $L_{i/i+1}$ further comprises two "on-off" valves denoted $V_i$ and $V_{i+1}$.

$V_i$ is placed between the plate $P_i$ and the connections to the injection and withdrawal lines, and $V_{i+1}$ is placed between the connections to the injection and withdrawal lines and the plate $P_{i+1}$.

Figure 1:
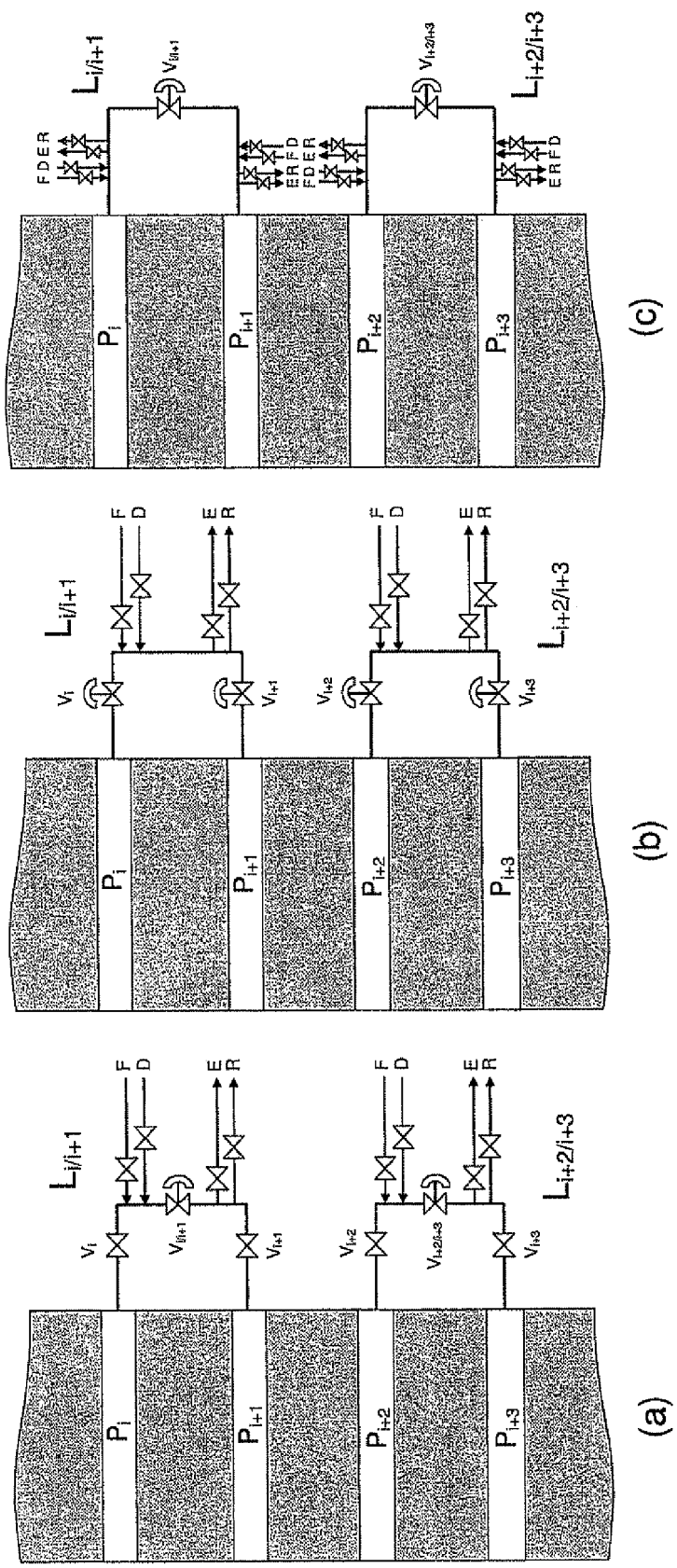
FIG. 1a represents a portion of the simulated moving bed (SMB) device of the invention comprising five beds separated by four distributor plates denoted $P_i$, $P_{i+1}$, $P_{i+2}$ and $P_{i+3}$, said four distributor plates being connected in pairs by two bypass lines $L_{i/i+1}$ and $L_{i+2/i+3}$. Each bypass line comprises the same means. The line $L_{i/i+1}$ comprises a connection to a feed F injection line, a connection to a desorbant D injection line, a connection to an extract E withdrawal line and a connection to a raffinate R withdrawal line.

FIG. 1b represents a portion of a variation of a simulated moving bed device (SMB) of the invention comprising five beds separated by four distributor plates denoted $P_i$, $P_{i+1}$, $P_{i+2}$ and $P_{i+3}$, these four distributor plates being connected in pairs via two bypass lines $L_{i/i+1}$ and $L_{i+2/i+3}$. Each bypass line comprises the same means.

The line $L_{i/i+1}$ comprises a connection to a feed F injection line, a connection to a desorbant D injection line, a connection to an extract E withdrawal line and a connection to a raffinate R withdrawal line.

The bypass line $L_{i/i+1}$ further comprises two regulating valves $V_i$ and $V_{i+1}$.

$V_i$ is placed between the plate $P_i$ and the connections to the injection and withdrawal lines, and $V_{i+1}$ is placed between the connections to the injection and withdrawal lines and the plate $P_{i+1}$.

FIG. 1c represents a portion of another variation of a simulated moving bed device (SMB) of the invention comprising five beds separated by four distributor plates denoted $P_i$, $P_{i+1}$, $P_{i+2}$ and $P_{i+3}$, these four distributor plates being connected in pairs via two bypass lines $L_{i/i+1}$ and $L_{i+2/i+3}$. Each bypass line comprises the same means. The line $L_{i/i+1}$ comprises two connections to two feed F injection lines, two connections to two desorbant D injection lines, two connections to two extract E withdrawal lines and two connections to two raffinate R withdrawal lines.

The connections to the injection and withdrawal lines are divided into two groups, one located upstream, the other downstream of the bypass line $L_{i/i+1}$.

Each group comprises a connection to a line for injection of feed F, for injection of desorbant D, for withdrawal of extract E and for withdrawal of raffinate R.

The bypass line $L_{i/i+1}$ further comprises a regulating valve $V_{i/i+1}$ located between the connections to the upstream injection and withdrawal lines on the one hand, and the connections to the downstream injection and withdrawal lines of the bypass line on the other hand.

Figure 2:
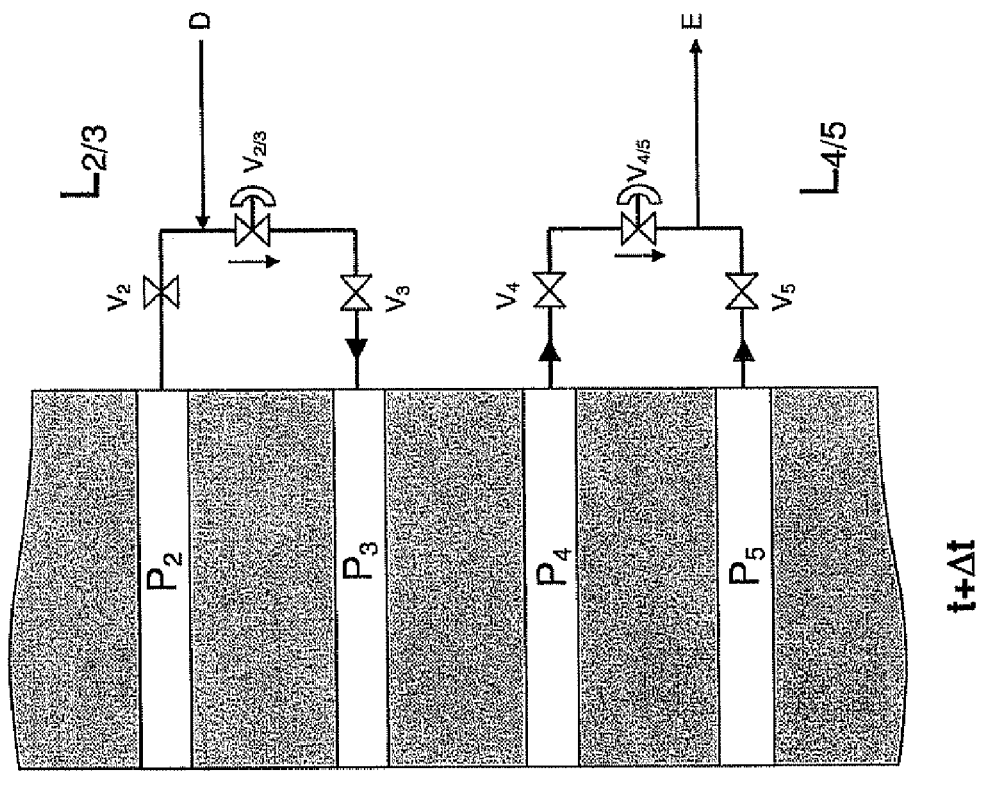
Figure 2:
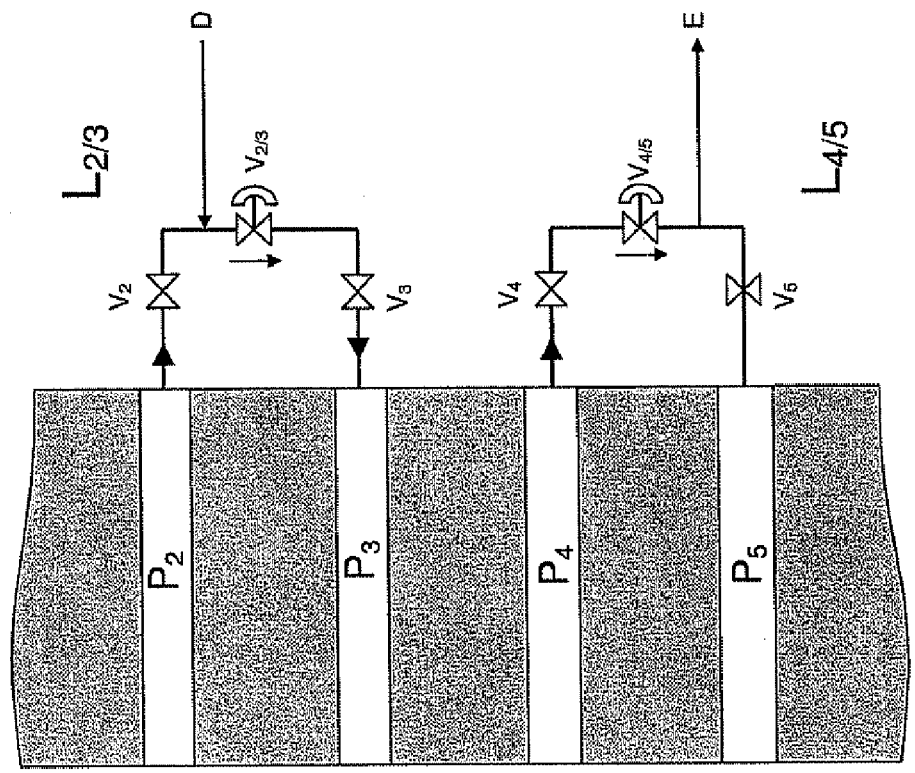

FIG. 2 represents a portion of the first variation of the simulated moving bed device in operation. This portion of the device comprises four distributor plates denoted $P_2$, $P_3$, $P_4$ and $P_5$.

The first portion of FIG. 2 shows a configuration at time t during which desorbant D is injected onto the plate $P_2$ while regulating the flushing flow rate in the second portion of the bypass line $L_{2/3}$. Again at time t, extract E is withdrawn from plate $P_4$, and there is no flow in the second portion of the bypass line $L_{4/5}$.

The second portion of FIG. 2 shows the preceding configuration one switch period after time t (i.e. at t+Δt). Desorbant D is injected onto the plate $P_3$ and there is no flow in the first portion of the bypass line $L_{2/3}$. Still at this time, i.e. t+Δt, extract E is withdrawn from the plate $P_5$ while regulating the flushing flow rate in the first portion of the bypass line $L_{4/5}$.

Figure 3:
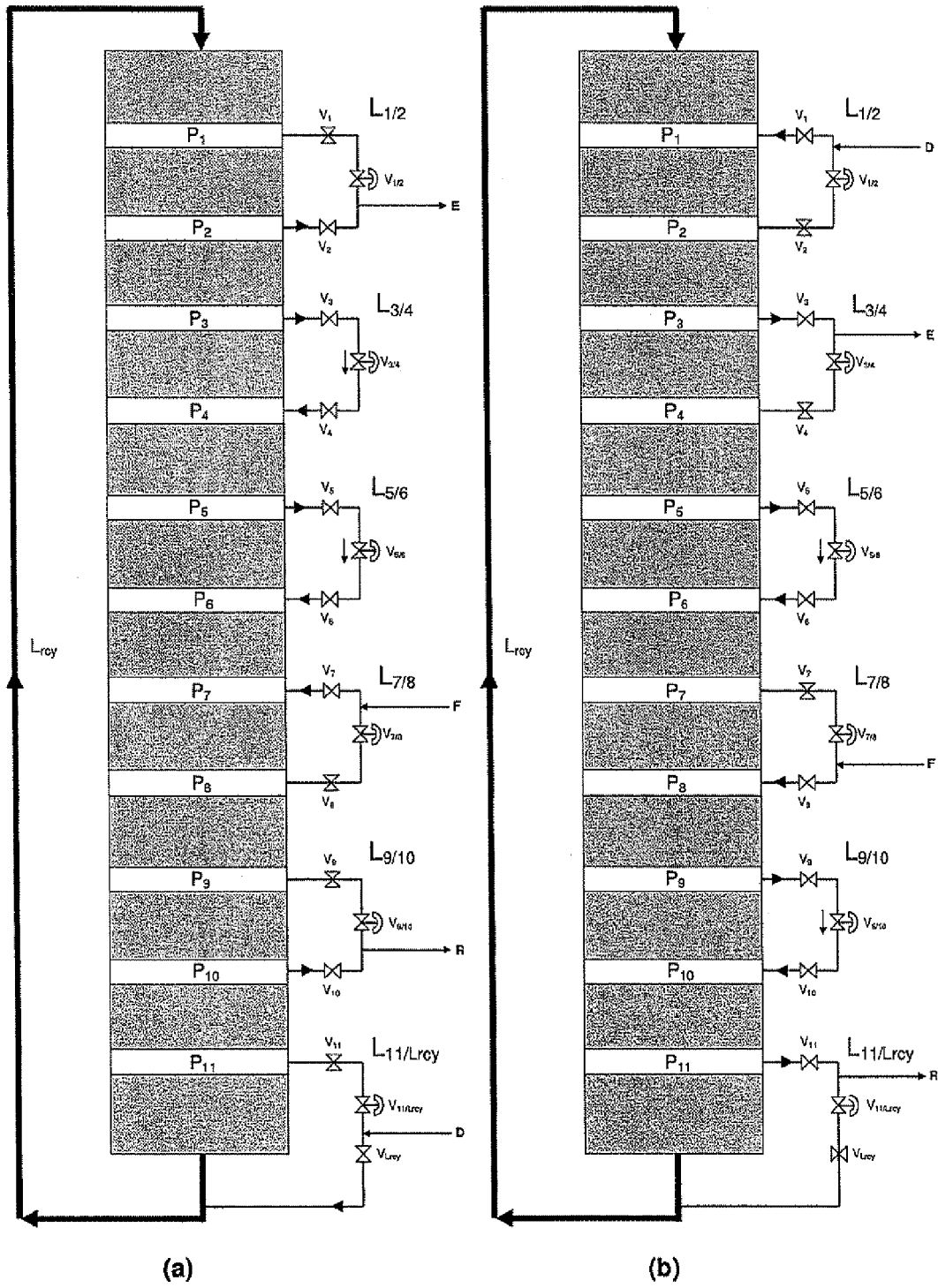

FIG. 3 shows the simulated moving bed device of the prior art constituted by 12 beds in operation.

FIG. 3a corresponds to the first step of the cycle.

FIG. 3b corresponds to the second step of the cycle.

Figure 4:
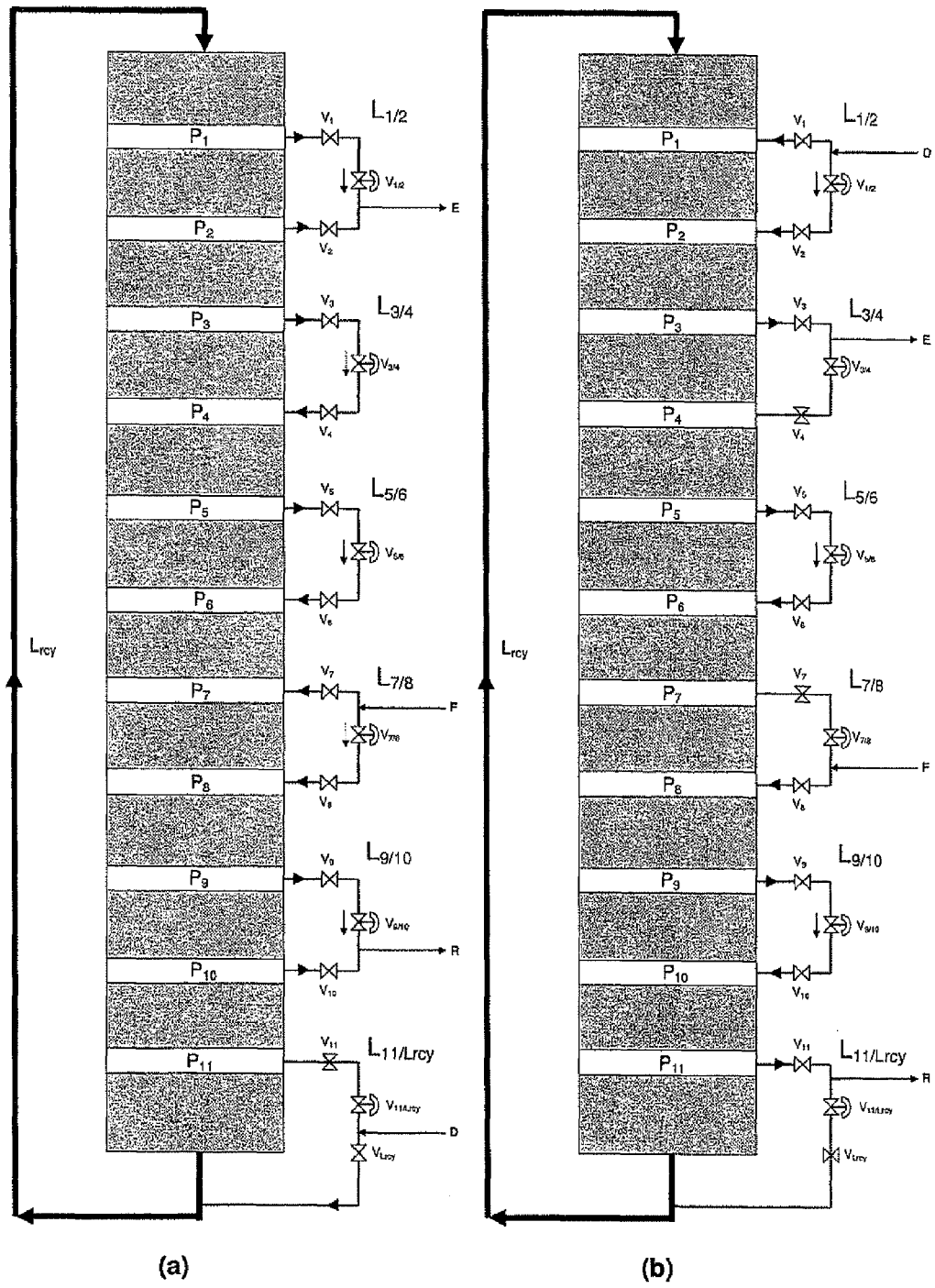

FIG. 4 shows a simulated moving bed device of the invention constituted by 12 beds in operation.

FIG. 4a corresponds to the first step of the cycle.

FIG. 4b corresponds to the second step of the cycle.

SIMPLIFIED DESCRIPTION OF THE INVENTION

The present invention concerns a method for managing the bypass lines of a device comprising external bypass lines $L_{i/i+1}$ directly joining two successive plates, $P_i$ termed the upstream plate and $P_{i+1}$ termed the downstream plate, the index "i" being either even or (exclusively of the foregoing) odd, along the whole length of the column.

By way of clarification, in a first case the bypass lines connect the plates $P_2$ and $P_3$, $P_4$ and $P_5$, $P_6$ and $P_7$ and so on.

In the other case, the bypass lines connect the plates $P_1$ and $P_2$, $P_3$ and $P_4$, $P_5$ and $P_6$ and so on.

The bypass lines connected to an injection line or withdrawal line in operation should be distinguished from the bypass lines which are not connected to any injection or withdrawal line in operation.

Regarding the bypass lines which are not connected to any injection or withdrawal line in operation, the rules regulating the flow rates in the bypass lines as defined in application 09/01784 are continued to be applied.

The present invention applies solely to the bypass lines which are connected to an injection or withdrawal line in operation and consists of, in certain cases, establishing a flushing flow on said bypass lines.

This flushing flow, when it is in place in a bypass line connected to an injection line in operation, is thus constituted by a portion of said injection flow.

This flushing flow, when it is in place in a bypass line connected to a withdrawal line in operation, thus constitutes a portion of said withdrawal flow.

Two cases can be distinguished; they form the subject matter of the invention:

a) the case in which feed or desorbant is injected onto a plate termed the upstream plate in the direction defined above;

b) the case in which extract or raffinate is withdrawn from a downstream plate in the direction defined above.

For a better understanding of the device of the invention, two portions have to be distinguished on a bypass line $L_{i/i+1}$ connecting an upstream plate $P_i$ to a downstream plate $P_{i+1}$:

a first portion included between the plate $P_i$ located upstream of said bypass line and the connection point with the injection or withdrawal line;

a second portion included between the connection point with the injection line or withdrawal line and the plate $P_{i+1}$ located downstream of said bypass line.

The two rules constituting the present invention may then be stated as follows:

a) when feed or desorbant is injected onto an upstream plate $P_i$, a flushing flow is introduced into the second portion of the bypass line, said flushing flow being regulated about a value equal to 50% of the synchronicity flow rate plus or minus 5%, and in the first portion of the bypass line, the injection flow rate is corrected by being equal to the flow rate for injection of feed or desorbant reduced by the value for the flushing flow introduced into the second portion of the bypass line;

b) when extract or raffinate is withdrawn from a downstream plate $P_{i+1}$, a flushing flow is introduced into the first portion of the bypass line, said flushing flow being regulated to a value equal to 50% of the synchronicity flow rate plus or minus 5%, and in the second portion of the bypass line, the withdrawal flow rate is corrected by being equal to the flow rate for withdrawal of the extract or raffinate reduced by the value of the flow rate of the flush introduced into the first portion of the bypass line.

The synchronicity flow rate is defined as $(V_i + V_{i+1} + VL_{i/i+1})/ST$, in which expression:

$V_i$ denotes the volume of the distribution/extraction system of the upstream plate $P_i$;

$V_{i+1}$ denotes the volume of the distribution/extraction system of the downstream plate $P_{i+1}$;

$VL_{i/i+1}$ denotes the volume of the bypass line between $P_i$ and $P_{i+1}$;

and ST denotes the switch time.

It has been discovered, relatively surprisingly, that establishing flushing flows in accordance with rules a) and b) can produce a significant gain in the yield of the desired product, as will be illustrated in the example below.

In accordance with a first variation of the present invention, the total number of beds of the SMB unit is 12 and is distributed as follows in the various zones:

2 beds in zone 1;
5 beds in zone 2;
3 beds in zone 3;
2 beds in zone 4.

In a second variation of the present invention, the total number of beds of the SMB unit is 15 and they are distributed in the various zones as follows:

3 beds in zone 1;
6 beds in zone 2;
4 beds in zone 3;
2 beds in zone 4.

The process of the invention may be applied to the separation of para-xylene in a mixture of aromatic C8 hydrocarbons.

The process of the invention may also be applied to the separation of meta-xylene in a mixture of aromatic C8 hydrocarbons.

DETAILED DESCRIPTION OF THE INVENTION

The invention concerns an improved simulated moving bed separation device.

More precisely, the invention is in the field of SMB units with a single chamber for injection or withdrawal of the various fluids, each plate being divided into a certain number of panels, and each panel being equipped with a chamber for injection and withdrawal of fluids.

In addition, the SMB units of the present invention are units in which the bypass lines connect two consecutive plates, namely $P_i$ and $P_{i+1}$, but the index "i" is either even or (exclusively of the foregoing) odd, along the whole length of the column. Thus, by considering any index "i" (even or odd), a plate $P_i$ is connected via a bypass line either to plate $P_{i+1}$ or (exclusively of the foregoing) to plate $P_{i-1}$.

FIG. 1a shows a bypass line $L_{i/i+1}$ which can connect the upstream plate $P_i$ to the downstream plate $P_{i+1}$. This bypass line $L_{i/i+1}$ comprises connections to lines for injection of feed F and desorbant D and to lines for withdrawal of extract E and raffinate R.

The connections to the injection lines are located upstream of the connections to the withdrawal lines. Between the connections to the injection lines and the connections to the withdrawal lines is a regulating valve $V_{i/i+1}$. The bypass line $L_{i/i+1}$ also comprises two on-off valves denoted $V_i$ and $V_{i+1}$. $V_i$ is placed between the plate $P_i$ and the connections to the injection and withdrawal lines, and $V_{i+1}$ is located between the connections to the injection and withdrawal lines and the plate $P_{i+1}$.

In a variation of the device of the invention (FIG. 1b), the bypass line $L_{i/i+1}$ comprises no on-off valves nor a regulating valve located between the connections to the injection lines and the connections to the withdrawal lines, but comprises two regulating valves $V_i$ and $V_{i+1}$.

$V_i$ is placed between the plate $P_i$ and the connections to the injection and withdrawal lines;

$V_{i+1}$ is placed between the connections to the injection and withdrawal lines and the plate $P_{i+1}$.

It has surprisingly been discovered that the ideal function of the bypass lines connected to the injection or withdrawal lines in operation necessitates establishing a certain flushing flow in a portion of said bypass lines.

Two portions of the bypass line $L_{i/i+1}$ can be distinguished:

a first portion included between the plate $P_i$ located upstream of said bypass line and the connection point with the injection or withdrawal line;

a second portion included between the connection point with the injection or withdrawal line and the plate $P_{i+1}$ located downstream of said bypass line.

When feed or desorbant is injected onto the plate $P_i$, in the upstream position, said plate $P_i$ being connected to the plate $P_{i+1}$ via a bypass line $L_{i/i+1}$, in contrast to that which was disclosed in the prior art, the bypass line $L_{i/i+1}$ must not be closed, but in contrast the flushing flow rate which flows in the second portion of the bypass line is modulated to rinse the plate $P_{i+1}$.

This flow rate must be regulated in order to correspond to approximately 50% of the synchronicity. The corrected injection flow flowing in the first portion of the bypass line $L_{i/i+1}$ is then equal to the injection flow rate of the feed or desorbant reduced by the flow rate of the flush flowing in the second portion of the bypass line.

When feed or desorbant is injected onto a plate $P_{i+1}$, in the downstream position, said plate $P_{i+1}$ being connected to the plate $P_i$ via a bypass line $L_{i/i+1}$, then said bypass line must then be closed. The flow rate in the second portion of the bypass line is then equal to the injection flow rate of feed or desorbant.

FIG. 2 shows the case in which a flushing flow exists during the injection of desorbant D onto the bypass line $L_{2/3}$ at time t. The description below is based on the configuration of the bypass line which comprises a regulating valve $V_{i/i+1}$ and two valves $V_i$ and $V_{i+1}$ (FIG. 1a).

Desorbant D is injected onto the bypass line $L_{2/3}$ so as to inject a stream onto the plate $P_2$ which is the plate located upstream of the bypass line $L_{2/3}$. The regulating valve $V_{2/3}$ can thus regulate the flushing flow composed of desorbant D, the on-off valves $V_2$ and $V_3$ being open. This flushing flow can rinse plate $P_3$.

At time t+Δt (Δt being the switch time), injection of flow D is carried out on the bypass line $L_{2/3}$ so as to inject a stream onto the plate $P_3$ which is the plate located downstream of the bypass line $L_{2/3}$. In this case, the on-off valve $V_2$ is closed and the valve $V_3$ is open such that there is only a flow in the second portion of the bypass line $L_{2/3}$.

Similarly, when extract or raffinate is withdrawn from a plate $P_{i+1}$, said plate $P_{i+1}$ being connected to the plate $P_i$ via a bypass line $L_{i/i+1}$, in contrast to that disclosed in the prior art, the bypass line must not be closed, but in contrast the flushing flow which flows in the first portion of the bypass line $L_{i/i+1}$ is modulated, allowing the contents of the plate $P_i$ to be withdrawn.

This flow must be regulated in order to correspond to approximately 50% of the synchronicity. The corrected withdrawal flow flowing in the second portion of the bypass line $L_{i/i+1}$ is then equal to the flow rate of extract or raffinate withdrawal reduced by the flow rate of the flush flowing in the first portion of the bypass line.

When extract or raffinate is withdrawn from a plate $P_i$, said plate $P_i$ being connected to the plate $P_{i+1}$ via a bypass line $L_{i/i+1}$, said bypass line must be closed.

FIG. 2 shows the case in which there is a flushing flow during withdrawal of extract E on the bypass line $L_{4/5}$ at time t+Δt. The description below is based on the configuration of the bypass line which comprises a regulating valve $V_{i/i+1}$ and two valves $V_i$ and $V_{i+1}$ (FIG. 1a).

At time t, extract E is withdrawn in bypass line $L_{4/5}$ so as to withdraw a stream at plate $P_4$ which is the plate located upstream of the bypass line $L_{4/5}$. The on-off valve $V_5$ is thus closed, the on-off valve $V_4$ is open such that there is only flow in the first portion of the bypass line $L_{4/5}$. At time t+Δt (Δt being the switch time), the extract E is withdrawn on the bypass line $L_{4/5}$ so as to withdraw a stream from the plate $P_5$ which is the plate located downstream of the bypass line $L_{4/5}$. In this case, the regulating valve $V_{4/5}$ is used to regulate the flushing flow rate removed from plate $P_4$ and the on-off valves $V_4$ and $V_5$ are open.

More precisely, the present invention can be defined as a process for simulated moving bed (SMB) separation of a feed F in a SMB device having at least one column, said column being composed of a plurality of beds of adsorbent separated by plates $P_i$ each comprising an injection/withdrawal system, in which process the feed F and a desorbant D are injected and at least one extract E and at least one raffinate R are withdrawn, the injection and withdrawal points being shifted over time by a value corresponding to one bed of adsorbent with a switch time ST, and determining a plurality of operational zones of the SMB, and in particular the following 4 principal zones:
  a zone 1 included between the injection of the desorbant D and the withdrawal of extract E;
  a zone 2 included between the withdrawal of the extract E and the injection of the feed F;
  a zone 3 included between the injection of the feed F and the withdrawal of the raffinate R;
  a zone 4 included between the withdrawal of the raffinate R and the injection of the desorbant D;
the device further comprising external bypass lines $L_{i/i+1}$ directly joining two successive plates, $P_i$ termed the upstream plate and $P_{i+1}$ termed the downstream plate, the index "i" being either even or (exclusively of the foregoing) odd, along the whole length of the column, and allowing flushing of said plates, in which device the bypass lines $L_{i/i+1}$ are differentiated into two portions:
  a first portion included between the plate $P_i$ located upstream of said bypass line and the connection point with the injection or withdrawal line;
  a second portion included between the connection point with the injection or withdrawal line and the plate $P_{i+1}$ located downstream of said bypass line;
in which device each of the bypass lines $L_{i/i+1}$ comprises automated means for regulating the flushing flows in the bypass line, said flushing flows being established when the bypass line is connected to an injection or withdrawal line in operation in accordance with the following two rules:
  a) when feed or desorbant is injected onto an upstream plate $P_i$, a flushing flow is introduced into the second portion of the bypass line, said flushing flow being regulated about a value equal to 50% of the synchronicity flow rate plus or minus 5%, and in the first portion of the bypass line, the injection flow rate is corrected by being equal to the flow rate for injection of feed or desorbant reduced by the value for the flushing flow introduced into the second portion of the bypass line;
  b) when extract or raffinate is withdrawn from a downstream plate $P_{i+1}$, a flushing flow is introduced into the first portion of the bypass line, said flushing flow being regulated to a value equal to 50% of the synchronicity flow rate plus or minus 5%, and in the second portion of the bypass line, the withdrawal flow rate is corrected by being equal to the flow rate for withdrawal of the extract or raffinate reduced by the value of the flow rate of the flush introduced into the first portion of the bypass line.

The synchronicity flow rate is defined as $(V_i+V_{i+1}+VL_{i/i+1})/ST$, in which expression:
  $V_i$ denotes the volume of the distribution/extraction system of the leaving plate $P_i$;
  $V_{i+1}$ denotes the volume of the distribution/extraction system of the arrival plate $P_{i+1}$;
  $VL_{i/i+1}$ denotes the volume of the bypass line between $P_i$ and $P_{i+1}$;
  and ST denotes the switch time.

The supersynchronicity is defined by the formula:

Supersynchronicity=actual flow rate in the bypass line under consideration/synchronicity flow rate−1

EXAMPLES

The invention will be better understood from the following examples.

Consider a SMB unit constituted by 12 beds, with a length of 1.1 m and an internal radius of 3.5 m, with a feed injection, a desorbant injection (could also be termed the eluent or solvent), an extract withdrawal and a raffinate withdrawal.

The plates have a single injection/withdrawal chamber.

The total volume is defined as $(V_i+V_{i+1}+VL_{i/i+1})$ where $VL_{i/i+1}$ is the volume of the bypass line from plate $P_i$ to plate $P_{i+1}$ and in which $V_i$ is the volume of the distribution/extraction system of plate $P_i$, and where $V_{i+1}$ is the volume of the distribution/extraction system of plate $P_{i+1}$.

The total volume represents 3% of the volume of the bed included between the plate $P_i$ and the plate $P_{i+1}$.

The beds are distributed in the configuration 2/5/3/2, i.e. the distribution of the beds is as follows:
  2 beds in zone 1;
  5 beds in zone 2;

3 beds in zone 3;
2 beds in zone 4.

The adsorbant employed is a zeolite of type BaX, and the eluent is para-diethylbenzene.

The temperature is 175° C. and the pressure is 15 bar.

The feed is composed of 20% para-xylene, 24% ortho-xylene, 51% meta-xylene and 5% ethylbenzene.

The switch time used is 141.6 seconds.

Thus, a complete cycle of the process comprises 12 steps.

The liquid flow rates for injection of the feed and desorbant are as follows:

204.1 m$^3 \cdot$h$^{-1}$ for the feed;
224.5 m$^3 \cdot$h$^{-1}$ for the desorbant;
i.e. a solvent ratio S/F=1.1.

The flow rate in zone 1 is 888.9 m$^3 \cdot$h$^{-1}$ and the extract flow rate is 96.8 m$^3 \cdot$h$^{-1}$.

All of the flow rates are given in m$^3 \cdot$h$^{-1}$ at a reference temperature of 25° C.

The flow rates in the bypass lines which are not connected to any injection or withdrawal line in operation are regulated to 120% of synchronicity in zone 2 and to 125% of synchronicity in zone 3.

Since zones 1 and 4 are constituted by 2 beds, each bypass line located in these zones is necessarily connected to an injection line or withdrawal line in operation.

Example 1

In Accordance with the Prior Art

In the prior art consisting of closing the bypass lines when the bypass lines are connected to injection or withdrawal lines in operation, on simulation, a para-xylene purity of 99.72% and a para-xylene yield of 83.8% is obtained.

FIG. 3a shows the first step of the cycle and FIG. 3b shows the second step of the cycle of a prior art simulated moving bed device.

The flow rates in each portion of the bypass lines during the 12 steps constituting the cycle of the process are given in Table 1 below.

The negative values in Table 1 below correspond to counter-current flows compared with the flow in the bypass line when that line is not connected to any injection or withdrawal line in operation.

Example 2

In Accordance with the Invention

In accordance with the invention, consisting of regulating, in certain cases, a flushing flow in the bypass lines connected to injection or withdrawal lines in operation in accordance with the rules defined above (the flow rate being regulated to a value corresponding to 50% of the synchronicity), by simulation a para-xylene purity of 99.76% and a para-xylene yield of 85.3% is obtained.

FIG. 4a shows the 1$^{st}$ step of the cycle and FIG. 4b shows the second step of the cycle for the simulated moving bed device of the invention.

The flow rates in each portion of the bypass lines during the 12 steps constituting the cycle of the process are given in Table 2 below.

In Table 2 below, the values for the flushing flows are shown in bold.

This flushing flow rate was 16.6 m$^3$/h.

The negative values in Table 2 below correspond to flows which are counter-current to the flow in the bypass line when that line is not connected to any injection or withdrawal line in operation.

TABLE 1

| | $L_{1/2}$ | | $L_{3/4}$ | | $L_{5/6}$ | | $L_{7/8}$ | | $L_{9/10}$ | | $L_{11/Lrcy}$ | |
|---|---|---|---|---|---|---|---|---|---|---|---|---|
| | 1$^{st}$ portion | 2$^{nd}$ portion | 1$^{st}$ portion | 2$^{nd}$ portion | 1$^{st}$ portion | 2$^{nd}$ portion | 1$^{st}$ portion | 2$^{nd}$ portion | 1$^{st}$ portion | 2$^{nd}$ portion | 1$^{st}$ portion | 2$^{nd}$ portion |
| 1$^{st}$ step | 0 | −96.7 | 39.8 | 39.8 | 39.8 | 39.8 | −204.1 | 0 | 0 | −331.9 | 0 | 224.5 |
| 2$^{nd}$ step | −224.5 | 0 | 96.7 | 0 | 39.8 | 39.8 | 0 | 204.1 | 41.5 | 41.5 | 331.9 | 0 |
| 3$^{rd}$ step | 0 | 224.5 | 0 | −96.7 | 39.8 | 39.8 | 39.8 | 39.8 | −204.1 | 0 | 0 | −331.9 |
| 4$^{th}$ step | 331.9 | 0 | −224.5 | 0 | 96.7 | 0 | 39.8 | 39.8 | 0 | 204.1 | 41.5 | 41.5 |
| 5$^{th}$ step | 0 | −331.9 | 0 | 224.5 | 0 | −96.7 | 39.8 | 39.8 | 39.8 | 39.8 | −204.1 | 0 |
| 6$^{th}$ step | 41.5 | 41.5 | 331.9 | 0 | −224.5 | 0 | 96.7 | 0 | 39.8 | 39.8 | 0 | 204.1 |
| 7$^{th}$ step | −204.1 | 0 | 0 | −331.9 | 0 | 224.5 | 0 | −96.7 | 39.8 | 39.8 | 39.8 | 39.8 |
| 8$^{th}$ step | 0 | 204.1 | 41.5 | 41.5 | 331.9 | 0 | −224.5 | 0 | 96.7 | 0 | 39.8 | 39.8 |
| 9$^{th}$ step | 39.8 | 39.8 | −204.1 | 0 | 0 | −331.9 | 0 | 224.5 | 0 | −96.7 | 39.8 | 39.8 |
| 10$^{th}$ step | 39.8 | 39.8 | 0 | 204.1 | 41.5 | 41.5 | 331.9 | 0 | −224.5 | 0 | 96.7 | 0 |
| 11$^{th}$ step | 39.8 | 39.8 | 39.8 | 39.8 | −204.1 | 0 | 0 | −331.9 | 0 | 224.5 | 0 | −96.7 |
| 12$^{th}$ step | 96.7 | 0 | 39.8 | 39.8 | 0 | 204.1 | 41.5 | 41.5 | 331.9 | 0 | −224.5 | 0 |

TABLE 2 in accordance with the invention

| | $L_{1/2}$ | | $L_{3/4}$ | | $L_{5/6}$ | | $L_{7/8}$ | | $L_{9/10}$ | | $L_{11/Lrcy}$ | |
|---|---|---|---|---|---|---|---|---|---|---|---|---|
| | 1st portion | 2nd portion | 1st portion | 2nd portion | 1st portion | 2nd portion | 1st portion | 2nd portion | 1st portion | 2nd portion | 1st portion | 2nd portion |
| 1st step | 16.6 | −80.1 | 39.8 | 39.8 | 39.8 | 39.8 | −187.5 | 16.6 | 16.6 | −315.3 | 0 | 224.5 |
| 2nd step | −207.9 | 16.6 | 96.7 | 0 | 39.8 | 39.8 | 0 | 204.1 | 41.5 | 41.5 | 331.9 | 0 |
| 3rd step | 0 | 224.5 | 16.6 | −80.1 | 39.8 | 39.8 | 39.8 | 39.8 | −187.5 | 16.6 | 16.6 | −315.3 |
| 4th step | 331.9 | 0 | −207.9 | 16.6 | 96.7 | 0 | 39.8 | 39.8 | 0 | 204.1 | 41.5 | 41.5 |
| 5th step | 16.6 | −315.3 | 0 | 224.5 | 16.6 | −80.1 | 39.8 | 39.8 | 39.8 | 39.8 | −187.5 | 16.6 |
| 6th step | 41.5 | 41.5 | 331.9 | 0 | −207.9 | 16.6 | 96.7 | 0 | 39.8 | 39.8 | 0 | 204.1 |
| 7th step | −187.5 | 16.6 | 16.6 | −315.3 | 0 | 224.5 | 16.6 | −80.1 | 39.8 | 39.8 | 39.8 | 39.8 |
| 8th step | 0 | 204.1 | 41.5 | 41.5 | 331.9 | 0 | −207.9 | 16.6 | 96.7 | 0 | 39.8 | 39.8 |
| 9th step | 39.8 | 39.8 | −187.5 | 16.6 | 16.6 | −315.3 | 0 | 224.5 | 16.6 | −80.1 | 39.8 | 39.8 |
| 10th step | 39.8 | 39.8 | 0 | 204.1 | 41.5 | 41.5 | 331.9 | 0 | −207.9 | 16.6 | 96.7 | 0 |
| 11th step | 39.8 | 39.8 | 39.8 | 39.8 | −187.5 | 16.6 | 16.6 | −315.3 | 0 | 224.5 | 16.6 | −80.1 |
| 12th step | 96.7 | 0 | 39.8 | 39.8 | 0 | 204.1 | 41.5 | 41.5 | 331.9 | 0 | −207.9 | 16.6 |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications, cited herein and of corresponding French application No. 10/00571, filed Feb. 11, 2010, are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for simulated moving bed (SMB) separation of a feed F carried out in a SMB device having at least one column, said column being composed of a plurality of beds of adsorbent separated by plates $P_i$ each comprising an injection/withdrawal system, in which process the feed F and a desorbant D are injected and at least one extract E and at least one raffinate R are withdrawn, the injection and withdrawal points being shifted over time by a value corresponding to one bed of adsorbent with a switch time ST, and determining a plurality of operational zones of the SMB, and in particular the following 4 principal zones:

a zone 1 included between the injection of the desorbant D and the withdrawal of extract E;

a zone 2 included between the withdrawal of the extract E and the injection of the feed F;

a zone 3 included between the injection of the feed F and the withdrawal of the raffinate R;

a zone 4 included between the withdrawal of the raffinate R and the injection of the desorbant D;

the device further comprising external bypass lines $L_{i/i+1}$ directly joining two successive plates, $P_i$ termed the upstream plate and $P_{i+1}$ termed the downstream plate, the index "i" being either even or (exclusively of the foregoing) odd, along the whole length of the column, and allowing flushing of said plates, in which device the bypass lines $L_{i/i+1}$ are differentiated into two portions:

a first portion included between the plate $P_i$ located upstream of said bypass line and the connection point with the injection or withdrawal line;

a second portion included between the connection point with the injection or withdrawal line and the plate $P_{i+1}$ located downstream of said bypass line;

in which device each of the bypass lines $L_{i/i+1}$ comprises automated means for regulating the flushing flows in said bypass line, said flushing flows being established when the bypass line is connected to an injection or withdrawal line in operation in accordance with the following two rules:

a) when feed or desorbant is injected onto an upstream plate $P_i$, a flushing flow is introduced into the second portion of the bypass line, said flushing flow being regulated about a value equal to 50% of the synchronicity flow rate plus or minus 5%, and in the first portion of the bypass line, the injection flow rate is corrected by being equal to the flow rate for injection of feed or desorbant reduced by the value for said flushing flow rate;

b) when extract or raffinate is withdrawn from a downstream plate $P_{i+1}$, a flushing flow is introduced into the first portion of the bypass line, said flushing flow being regulated to a value equal to 50% of the synchronicity flow rate plus or minus 5%, and in the second portion of the bypass line, the withdrawal flow rate is corrected by being equal to the flow rate for withdrawal of the extract or raffinate reduced by the value of said flush flow rate; the synchronicity flow rate being defined as $(V_i + V_{i+1} + VL_{i/i+1})/ST$, in which expression:

$V_i$ denotes the volume of the distribution/extraction system of the upstream plate $P_i$;

$V_{i+1}$ denotes the volume of the distribution/extraction system of the downstream plate $P_{i+1}$;

$VL_{i/i+1}$ denotes the volume of the bypass line between $P_i$ and $P_{i+1}$;

and ST denotes the switch time.

2. A simulated moving bed (SMB) separation process according to claim 1, wherein the total number of beds is 12, distributed as follows:

2 beds in zone 1;
5 beds in zone 2;
3 beds in zone 3;
2 beds in zone 4.

3. A simulated moving bed (SMB) separation process according to claim 1, wherein the total number of beds is 15, distributed as follows:

3 beds in zone 1;
6 beds in zone 2;
4 beds in zone 3;
2 beds in zone 4.

4. Application of a simulated moving bed separation process according to claim 1 to the separation of para-xylene in a mixture of aromatic C8 hydrocarbons.

5. Application of a simulated moving bed separation process according to claim 1 to the separation of meta-xylene in a mixture of aromatic C8 hydrocarbons.

* * * * *